Figure 1:
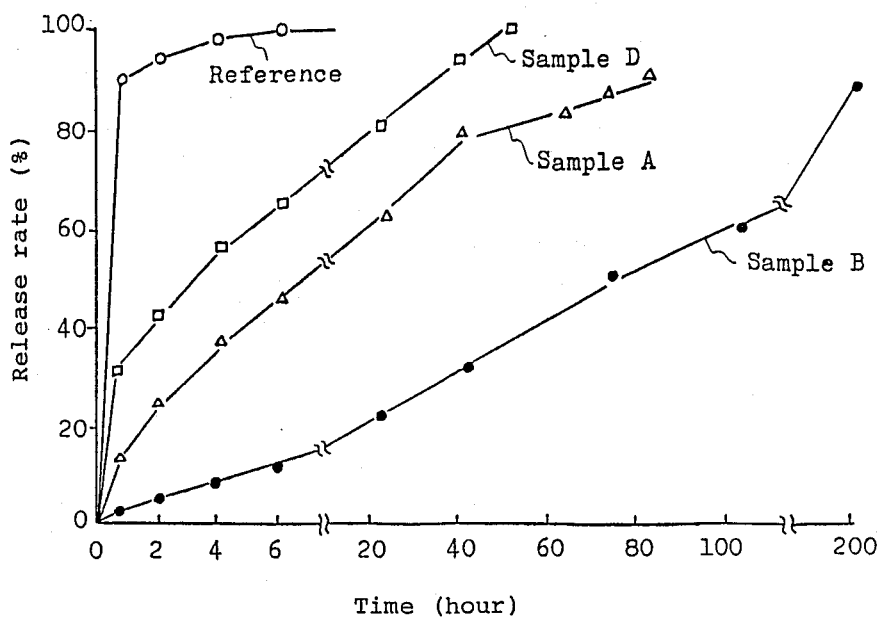

United States Patent [19]

Yamahira et al.

[11] Patent Number: 4,855,134

[45] Date of Patent: * Aug. 8, 1989

[54] SUSTAINED-RELEASE PREPARATION

[75] Inventors: Yoshiya Yamahira, Kobe; Keiji Fujioka, Amagasaki; Shigeji Sato, Ibaraki, all of Japan

[73] Assignee: Sumitomo Pharmaceuticals Company, Limited, Osaka, Japan

[*] Notice: The portion of the term of this patent subsequent to Sep. 27, 2005 has been disclaimed.

[21] Appl. No.: 855,387

[22] Filed: Apr. 24, 1986

Related U.S. Application Data

[63] Continuation-in-part of Ser. No. 660,045, Oct. 12, 1984, abandoned.

[30] Foreign Application Priority Data

Oct. 14, 1983 [JP] Japan ................... 58-193064
Nov. 1, 1983 [JP] Japan ................... 58-206226

[51] Int. Cl.$^4$ ............................................. A61K 45/02
[52] U.S. Cl. ..................... 424/85.7; 424/85.4
[58] Field of Search .......... 424/85, 85.4, 85.5, 424/85.6, 85.7

[56] References Cited

U.S. PATENT DOCUMENTS

| | | |
|---|---|---|
| 2,518,510 | 8/1947 | Welch . |
| 3,016,895 | 1/1962 | Sein . |
| 3,857,932 | 12/1974 | Shepherd et al. . |
| 4,181,731 | 1/1980 | Yoshida et al. ................ 424/27 B |
| 4,245,635 | 1/1981 | Kontos . |
| 4,347,234 | 8/1982 | Wahlig et al. . |
| 4,371,516 | 2/1983 | Gregory et al. ................ 424/422 |
| 4,442,051 | 4/1984 | Rowe et al. . |
| 4,465,622 | 8/1984 | Nobuhara et al. .................. 424/85 |
| 4,474,753 | 10/1984 | Hasham et al. ..................... 424/85 |
| 4,496,537 | 1/1985 | Kuan ................................. 424/85 |
| 4,503,035 | 3/1985 | Pestka et al. ...................... 424/85 |
| 4,536,387 | 8/1985 | Sakamoto et al. . |
| 4,604,284 | 8/1986 | Kusser et al. .................... 530/351 |
| 4,609,546 | 9/1986 | Herctoni ........................... 424/85 |

FOREIGN PATENT DOCUMENTS

| | | |
|---|---|---|
| 0094157 | 11/1983 | European Pat. Off. . |
| 0098110 | 1/1984 | European Pat. Off. . |
| 0134289 | 3/1985 | European Pat. Off. . |
| 3104815 | 2/1981 | Fed. Rep. of Germany . |
| 102519 | 8/1980 | Japan . |
| 0122317 | 9/1981 | Japan . |
| 642385 | 11/1947 | United Kingdom . |
| 2042888 | 10/1980 | United Kingdom . |
| 2067072 | 7/1981 | United Kingdom . |
| 2091554 | 1/1982 | United Kingdom . |
| 8301198 | 4/1983 | World Int. Prop. O. . |

*Primary Examiner*—Blondel Hazel
*Attorney, Agent, or Firm*—Birch, Stewart, Kolasch & Birch

[57] ABSTRACT

A sustained-release preparation of indomethacin or interferon comprising the active ingredient in admixture with a pharmaceutically acceptable biodegradable carrier, particularly a carrier selected from collagen, gelatin, and a mixture thereof. The preparation is particularly suitable for parenteral administration and can release the active ingredient in an effective amount for a long period of time.

14 Claims, 1 Drawing Sheet

SUSTAINED-RELEASE PREPARATION

This is a continuation-in-part application of U.S. Ser. No. 660,045 filed on Oct. 12, 1984, now abandoned.

The present invention relates to a sustainedrelease preparation of indomethacin or interferon in admixture with a pharmaceutically acceptable biodegradable carrier. More particularly, it relates to a sustainedrelease preparation comprising as an active ingredient indomethacin of the formula:

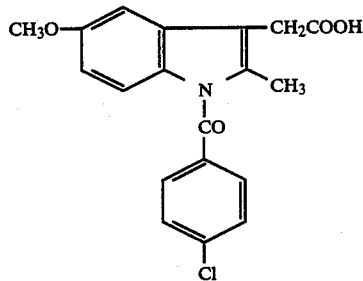

or a salt thereof or an analogous compound thereof, or interferon in admixture with a pharmaceutically acceptable biodegradable carrier. The sustained-release preparation can release the active ingredient when administered so that the effective level in blood or in a leasional region is maintained for a long period of time.

It is well known that indomethacin is a nonsteroidal antirheumatic and can show potent antiinflammatory action against local inflammation but it also shows undesirable side effect systemically in the central nervous system and in peptic organs. In the case when such a medicament is administered in a parenteral route, for the purpose of exhibiting the main action of the medicament while depressing the side effect, it has been required to develop a sustained-release preparation suitable for parenteral administration such as a sustained-release injection, but such a preparation has never been succeeded in development.

It is also known that interferon is a certain glycoprotein which is produced in cells of animals including humans by irritation with a virus or with any other substance and is very useful as an agent for inhibiting the growth of viruses and as an anti-tumor agent. Recently, clinical tests of interferon have been done for investigating the activities against various virus diseases and tumors, and it has been expected that the activities are promoted by sustaining the level in blood or in lesional regions of the medicament. However, such a sustained-release preparation suitable for parenteral administration has never been found.

The present inventors have intensively studied a sustained-release preparation of indomethacin or interferon which is clinically useful and have found that the desired sustained-release preparation can be obtained by admixing the active compound with a specific biodegradable carrier.

The present inventors have found that it is very difficult to sustain the release of the medicament, particularly interferon by known techniques for releasesustaining, because interferon is very unstable not only within the body but also in the preparation. Hence, the activity thereof is largely and rapidly decreased by the conventional release-sustaining techniques such as heat treatment or irradiation, or chemical treatments with organic solvents or aldehydes, and further, the conventional interferon preparations contain a very small amount of interferon which is water-soluble and hence interferon is easily and rapidly released when administered. Besides, the interferon preparation is a parenteral preparation such as injection, and hence, there is a problem of accumulation of the carrier within a body when the preparation is administered for a long period of time. From this viewpoint, a non-biodegradable carrier such as silicone which has recently been used in some medical sections can not be employed. The preparation of the present invention can overcome such various problems and can give the desired release-sustaining effect.

An object of the invention is to provide an improved sustained-release preparation of indomethacin or interferon. Another object of the invention is to provide a parenteral preparation of indomethacin or interferon which can gradually increase the active ingredient and can maintain the desired level of the active ingredient in blood or in a lesional region for a long period of time. A further object of the invention is to provide a sustained-release preparation using a specific biodegradable carrier which can be administered in a parenteral route without the problem of accumulation of carrier within the body. A still further object of the invention is to provide a method for preparing the sustained-release preparation as set forth above without using any specific binding agent and without heating. These and other objects and advantages of the present invention will be apparent to persons skilled in the art from the following description.

The sustained-release preparation of the present invention comprises as an active ingredient indomethacin or interferon in admixture with a pharmaceutically acceptable biodegradable carrier.

The biodegradable carrier used in the present invention means a carrier which can easily be absorbed or be subject to enzymolysis in body and can be implanted into the body. Suitable examples of the biodegradable carrier are proteins such as collagen, gelatin, and albumin, and the like. These substances can be used alone or in any combination of two or more thereof, but in view of moldability, collagen or gelatin or a mixture thereof are preferably used. Collagen is a protein which is a main protein of connective tissue of animals and has less antigenicity, and hence, has widely been used as safe operation yarn in various medical operations. The collagen may be an antelocollagen having far less antigenicity which is obtained by removing the telopeptide region by treating collagen with an enzyme (e.g. pepsin) in order to make it safer. Gelatin is a protein derived from collagen. Gelatin is a high molecular weight amphoteric electrolyte which has less antigenicity and properties of convertible between sol and gel forms and is cheap in cost, and hence it has already been confirmed as a safe substance for medical use.

The active ingredient used in the present invention includes indomethacin or a salt thereof and an analogous derivative thereof. It may also be used together with one or more other medical compounds which can show additional or synergistic activities with indomethacin. Other active ingredient used in the present invention is interferon, which may be used alone or in a combination with an interferon activator or together with one or more other medical compounds which can show additional or syntergistic activities with interferon. The interferon includes α-, β-, and γ-interferons, and a mixture thereof.

The medicaments and carriers used in the present invention are preferably purified products, but commercially available products may be used as they stand. The commercially available medicaments and carriers usually contain some appropriate additives such as stabilizers and buffering agents to some extent. For instance, an aqueous collagen solution contains usually a buffer of inorganic or organic salts, such as phosphate buffer, a citrate buffer or an acetate buffer. Commercially available interferons usually contain sodium chloride and further human serum albumin, amino acids (e.g. glycine, alanine, etc.), saccharides (e.g. glucose, etc.), sugar-alcohols (e.g. mannitol, xylitol, etc.). These products may be used as they stand, but in view of release-sustaining properties, it is preferable to remove such additives or other components.

The ratio of the carrier and the medicament is not critical but, for example, indomethacin is preferably incorporated in an amount of 0.005 to 1 mg per 1 mg of carrier, and interferon is preferably incorporated in an amount of $10^3$ to $10^8$ IU per 1 mg of carrier.

One of the characteristics of the present invention is in that the preparation can be prepared without using any specific binding agent and further without heat treatment through the steps and hence is particularly suitable for medicaments which are unstable to heat.

The sustained-release preparation of the present invention can be prepared by the following method.

An active ingredient or an aqueous solution thereof is mixed with a biodegradable carrier or an aqueous solution thereof, and the mixture is homogeneously mixed by stirring while preventing the occurrence of foam as much as possible. By the mixing of the active ingredient and the carrier in a liquid state, the active ingredient is incorporated into the carrier matrix. Thereafter, the mixture is dried. The drying method is not specified, but it may be dried, for example, by allowing to stand, or by spray-drying or lyophilization. Besides, the mixture may optionally be concentrated at a low temperature before drying, for example, by allowing to stand the solution at room temperature. In the above steps, the mixing step and drying step are usually carried out at room temperature or lower temperature and optionally under cooling. For instance, the mixing step is usualy carried out at about 5° C. to 30° C.; the drying by lyophilization is usually carried out at -50° C. to 0° C.; and the drying by allowing to stand or by spray-drying is usually carried out at room temperature or lower (i.e. about 15° C. to 30° C.). Besides, the spray-dry is usually carried out by controlling the temperature of the solution and vessel at room temperature or lower, by which the temperature of the active ingredient can be kept at room temperature or lower and hence no damage is given to the active ingredient even though it is unstable to heat.

The preparation of the present invention consists preferably, substantially of an active ingredient and a biodegradable carrier. That is, when components other than the active ingredient and carrier are present in the preparation of the invention, they occasionally promote the release of active ingredient, and hence, it is preferable not to incorporate such other components as much as possible. However, from the practical viewpoint, the preparation may contain other components from commercially available medicaments and carriers unless they affect substantially the release-sustaining properties. Likewise, the preparation of the invention may be incorporated by pharmaceutically acceptable conventional stabilizers, preservatives, and local anesthetic agents unless they affect substantially the release-sustaining properties.

The preparation thus obtained may be optionally processed so as make it fit the desired utilities. For example, the preparation is pulverized into powders under cooling with dry ice or liquid nitrogen so that the preparation is kept at about $-10°$ C. to about $-100°$ C., or by any other conventional pulverization methods at room temperature or lower temperature. The powder having a particle size suitable for injection may be suspended in a viscous solvent suitable for injection to give a sustained-release suspension for injection. Alternatively, the pulverized powder and the viscous solvent may be packed in the form of a kit, and they are mixed to prepare a suspension for injection when used. Suitable examples of the viscous solvent for injection are vegetable oils (e.g. peanut oil, cotton seed oil, sesame oil, castor oil, olive oil, corn oil, iodinated poppy seed oil fatty acids ethyl esters), polyethylene glycol, propylene glycol, silicon oil, medium-chain fatty acids triglycerides, or the like.

The preparation of the present invention contains the active ingredient in an amount in which the active ingredient is usually used. For example, indomethacin is usually contained in an amount of 0.5 to 500 mg preferable 1 to 200 mg, per dosage unit, and interferon is usually contained in an amount of $10^4$ to $10^9$ IU, preferable $10^5$ to $5 \times 10^8$ IU, per dosage unit.

In case of a preparation of indomethacin, the preparation thus obtained is useful for the treatment of various joint diseases by injection into a joint, by which the active ingredient can be maintained in a high local level.

Besides, the particles of the preparation as prepared by pulverization as mentioned above or by any other conventional pulverization methods may be compressed to form some specific shapes, such as a needle-like or fine bar-like shaped preparation (diameter: about 0.5 mm–1.5 mm, length: about 5 mm–15 mm), which can be inserted into a body by operation or with a forceps needle for fiberscope, an indwelling needle, or other appropriate administration device. Alternatively, the powdery preparation is previously entered into a mold, followed by concentrating at a low temperature or by lyophilizing to compress and form into a needle-like or a fine bar-like shaped preparation.

Moreover, the preparation of the present invention may be formed into specific shaped preparations such as pellet, spherical, hemispherical, button-like, granular or powdery shaped preparations, which can be implanted into the body or the lesional region in operation. The shapes to be formed may vary depending on the desired utilities and the desired degree of sustaining the activity of the medicament, and generally speaking, the shape of the preparation is larger, the time for sustaining of activity is longer.

Through whole steps for preparing the desired sustained-release preparations, the procedure is carried out under sterilized condition because the preparations are used as an injection or for implanting into a body. The preparation of the present invention may also be formed into other conventional sustained-release oral preparations, a medicine for external application, suppositories, or the like by conventional techniques.

The technique of the present invention can be applied to such a low molecular weight compound as indomethacin (molecular weight: 357.79) and also to a high molecular protein: interferon, and in both active ingredients, the desired level in blood or in the lesional region of the active ingredient can be maintained for a long period of time. This means that the technique of the present invention is applicable to various compounds having largely different properties, which is an epochal technique.

The present invention is illustrated by the following Experiments and Examples, but should not be construed to be limited thereto.

EXPERIMENT 1

In order to test the release rate of indomethacin from the sustained-release preparation of the present invention, the preparations of Examples 1, 2 and 4 disclosed hereinafter (Samples A, B and D) and a reference (indomethacin alone) were subjected to a release test by a rotary basket method with a basket stirring element as defined in U.S. Pharmacopeia.

The results are shown in the accompanying FIG. 1. In FIG. 1, Δ is a graph of Sample A, ● is that of Sample B, □ is that of Sample D, and o is that of reference (indomethacin alone). As is clear from the figure, in case of indomethacin alone, it was released immediately, but on the other hand, in the case of the preparation comprising indomethacin and collagen in a ratio of 1 : 1 by weight (Sample A), the releasing of the indomethacin was sustained for about 3 days, and in the case of the preparation comprising indomethacin and collagen in a ratio of 1 : 3 by weight (Sample B), it was sustained for about 8 days. Besides, in case of the preparation using gelatin as the carrier (Sample D), it was sustained for about one day.

EXPERIMENT 2

There were used as the test samples an oily suspension of interferon-collagen preparation prepared in Example 7 disclosed hereinafter (Sample G), a needle-shaped preparation of interferon-collagen prepared in Example 8 disclosed hereinafter (Sample H) and a reference (an aqueous injection of α-interferon originated from Namalwa cells). The test samples were each administered intramuscularly to rabbit, and the change of level in blood of the active ingredient with lapse of time was measured by RIA (radioimmunoassay) method. Two rabbits were used for each sample, and the test samples were each administered in a dose of $10^6$ U/kg. the number of blood level was shown in average in two rabbits.

Figure 2:
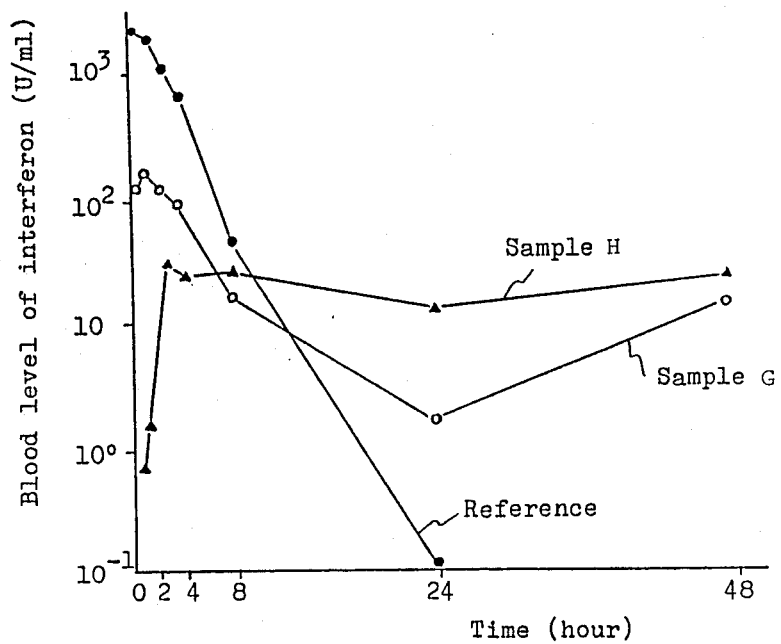

The results are shown in the accompanying FIG. 2. In FIG. 2, o is the graph of Sample G, ▲ is that of Sample H and ● is that of reference (α-interferon aqueous injection). As is clear from the figure, the Samples G and H showed release-sustaining, and even after 48 hours, the blood level of several tens unit/ml was maintained. The needle preparation showed particularly excellent release-sustaining.

Thus, it is also suggested by the test of in vivo using rabbits that the preparation of the present invention is useful clinically.

EXAMPLE 1

2 % antelocollagen (25 g) is dissolved in distilled water (100 ml), and indomethacin (0.5 g), is added thereto and the mixture is lyophilized to give a sustained-release preparation (A).

EXAMPLE 2

2 % atelocollagen (75 g) is dissolved in distilled water (300 ml), and indomethacin (0.5 g), is added thereto and the mixture is lyophilized to give a sustained-release preparation (B).

EXAMPLE 3

Gelatin (10 g) is dissolved in distilled water (100 ml), indomethacin (0.5 g), is added thereto and the mixture is lyophilized to give a sustained-release preparation (C).

EXAMPLE 4

The lyophilized product obtained in Example 3 is tabletted under reduced pressure to give a sustained-release preparation (D).

EXAMPLE 5

The lyophilized product obtained in Example 2 is pulverized at a low temperature using liquid nitrogen, and the powder is suspended in sesame oil to give an oily suspension preparation (E).

EXAMPLE 6

The lyophilized product obtained in Example 3 is pulverized at a low temperature using liquid nitrogen, and the powder is suspended in sesame oil to give an oily suspension preparation (F).

EXAMPLE 7

An aqueous solution of α-interferon (titer: 4.9 MU/ml, human serum albumin 1.5 mg/ml) (100 ml) and 2 % atelocollagen (50 g) are homogenously mixed with stirring while keeping the occurrence of foam as small as possible. The mixture is lyophilized and pulverized at a low temperature using liquid nitrogen. The pulverized product thus obtained is suspended in sesame oil to give an oily suspension type, sustained-release preparation (G) wherein interferon is contained in an amount of 4 MU per 1 vial.

EXAMPLE 8

The pulverized product in the same manner as described in Example 7 is formed under compression to give a needle-shaped sustained-release preparation (H) wherein interferon is contained in an amount of 10 MU per 1 needle.

EXAMPLE 9

The pulverized product in the same manner as described in Example 7 is suspended in castor oil to give an oily suspension type, sustained-release preparation wherein interferon is contained in an amount of 4 MU per 1 vial.

EXAMPLE 10

The pulverized product in the same manner as described in Example 7 is formed into a pellet shape under compression to give a pellet-shaped sustained-release preparation wherein interferon is contained in an amount of 10 MU per 1 pellet.

EXAMPLE 11

An aqueous solution of α-interferon (titer, 4.9 MU/ml) (100 ml) and atelocollagen powder (1 g) are mixed, and the resulting solution is entered into a mold and lyophilized. The lyophilized product is formed under compression to give a needle-shaped sustainedrelease preparation wherein interferon is contained in an amount of 10 MU per 1 needle.

EXAMPLE 12

The pulverized product prepared in the same manner as described in Example 7 is suspended in polyethylene glycol to give a suspension type, sustained-release preparation wherein interferon is contained in an amount of 4 MU per 1 vial.

EXAMPLE 13

The pulverized product prepared in the same manner as described in Example 7 is suspended in iodinated poppy seed oil fatty acids ethyl esters (sold by Libiodol Ultrafluid - Kodama Shoji) to give an oily suspension type, sustained-release preparation wherein interferon is contained in an amount of 4 MU per 1 vial.

What is claimed is:

1. A sustained-release preparation, which comprises interferon as an active ingredient and collagen as a carrier, said preparation being in the form of powder particles suspended in a viscous solvent suitable for injection, or being in the form of a shaped preparation suitable for use as an injection in a solid state or for implanting into a body.

2. The preparation according to claim 1, wherein interferon is α-interferon.

3. A sustained-release preparation which comprises interferon as an active ingredient and collagen as a carrier, said preparation being prepared by a process which comprises:
   a. mixing interferon and collagen to form a liquid mixture; and
   b. drying the resultant mixture.

4. The prepartion according to claim 3, wherein interferon is α-interferon.

5. The preparation according to claim 3, wherein said preparation contains interferon in an amount of $10^4$ to $10^9$ IU per dosage unit.

6. The preparation according to claim 1, wherein the form of the shaped prepartion is needle-like or fine bar-like having a diameter of about 0.5 mm to 1.5 mm and a length of about 5 mm to 15 mm.

7. The preparation according to claim 1, wherein the shaped preparation is in the form of a pellet, sphere, hemisphere, button, grain or powder.

8. The preparation according to claim 1, wherein a small amount of gelatin is also incorporated as the biodegradable carrier.

9. A method for the preparation of a sustained-release preparation of interferon, which comprises mixing interferon and collagen to form a liquid mixture and drying the resultant mixture.

10. The method according to claim 9, wherein the mixing step is conducted at a temperature of about 5° C. to 30° C.

11. The method according to claim 9, wherein the drying step is effected by lyophilization at a temperature of −50° C. to 0° C.

12. The method according to claim 9, wherein the dried mixture is pulverized to produce the powder particles.

13. The method according to claim 9, wherein the preparation is shaped by compressing the dried mixture or by allowing the dried mixture to stand in a mold until formed.

14. A sustained-release preparation which comprises interferon as an active ingredient and collagen as a carrier.

* * * * *